United States Patent [19]

Smythe

[11] 4,259,291
[45] Mar. 31, 1981

[54] METERING DEVICE

[75] Inventor: William J. Smythe, Canterbury, Conn.

[73] Assignee: Technicon Instruments Corporation, Tarrytown, N.Y.

[21] Appl. No.: 57,541

[22] Filed: Jul. 13, 1979

[51] Int. Cl.³ .......................... G01N 1/14; G01N 1/18; G01N 1/20
[52] U.S. Cl. .................................. 422/82; 73/423 A; 250/576; 356/410
[58] Field of Search .................. 422/82, 81, 103, 100; 356/410; 250/576; 23/230 R; 73/423 A

[56] References Cited

U.S. PATENT DOCUMENTS

| 3,479,141 | 11/1969 | Smythe et al. | 23/230 R |
| 3,843,326 | 10/1974 | Lichtenstenen | 422/82 |
| 3,929,413 | 12/1975 | Young et al. | 422/82 |
| 3,960,020 | 6/1976 | Gordon et al. | 73/423 A |
| 4,015,938 | 4/1977 | Jay | 422/82 |
| 4,121,466 | 10/1978 | Reichler et al. | 73/423 A |

Primary Examiner—R. E. Serwin
Attorney, Agent, or Firm—S. P. Tedesco

[57] ABSTRACT

Contamination between successive aqueous samples in a continuous-flow analytical system is eliminated by the careful and precise application of a thin, uniform film of immiscible fluid upon the outer surface of an aspirating probe of a metering system. The immiscible fluid is selected to preferentially wet the inner and outer probe surfaces and the inner wall surfaces of the conduits of such system, to the substantial exclusion of the aqueous samples. The immiscible fluid is aspirated, along with an air segment, between aspirations of successive samples, each aspirated air and sample segments are encapsulated by such immiscible fluid while passed through such system. A selective valve is utilized to isolate and transfer each fluid sample from the probe to such system.

19 Claims, 11 Drawing Figures

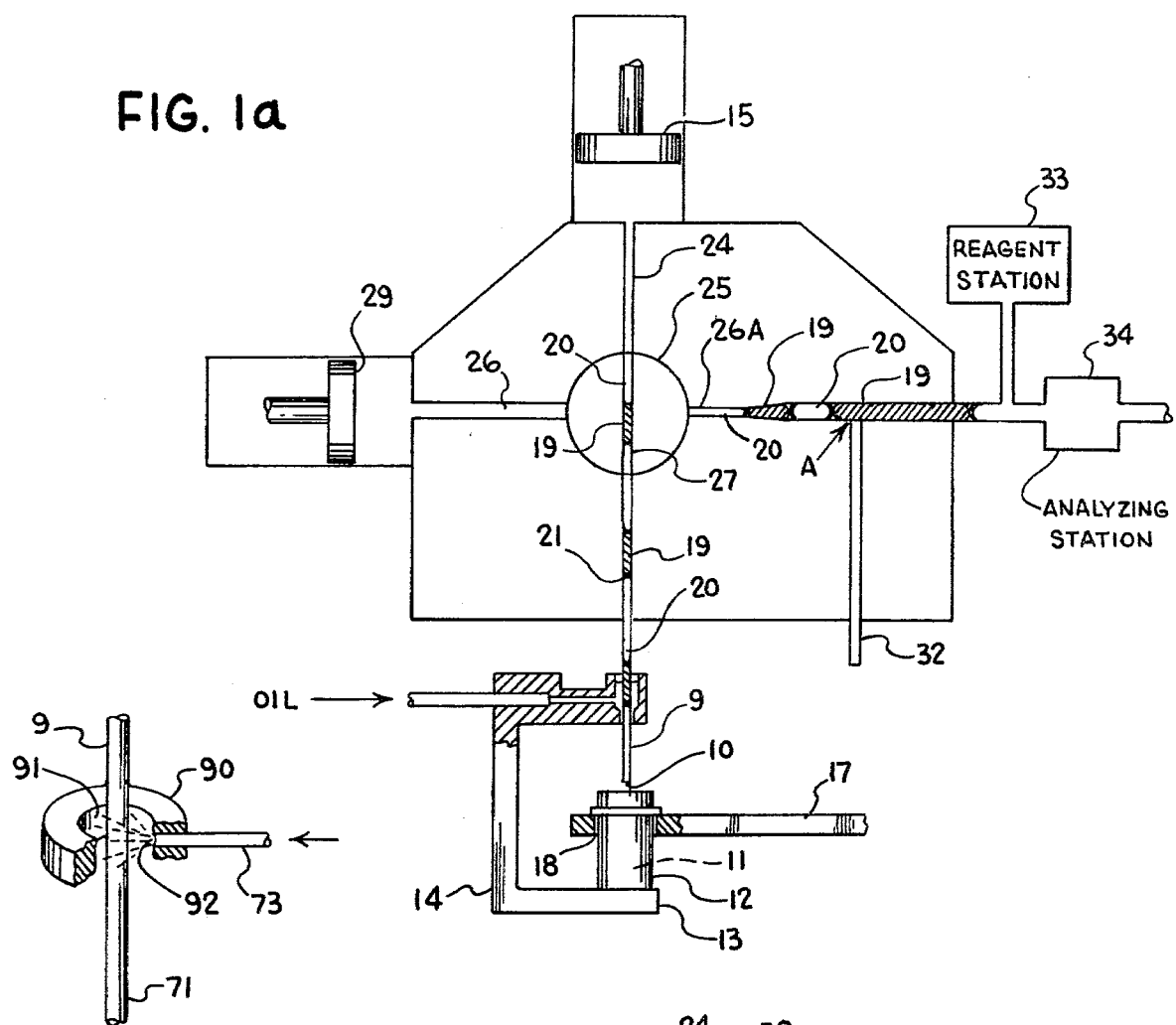
FIG. 1a
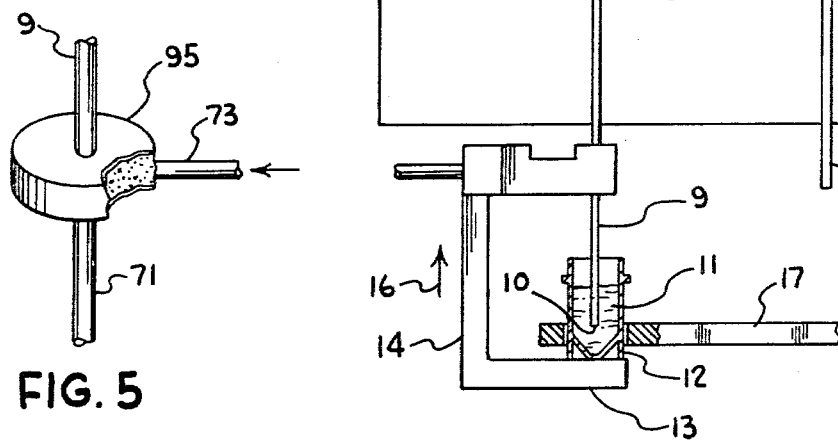
FIG. 4
FIG. 5
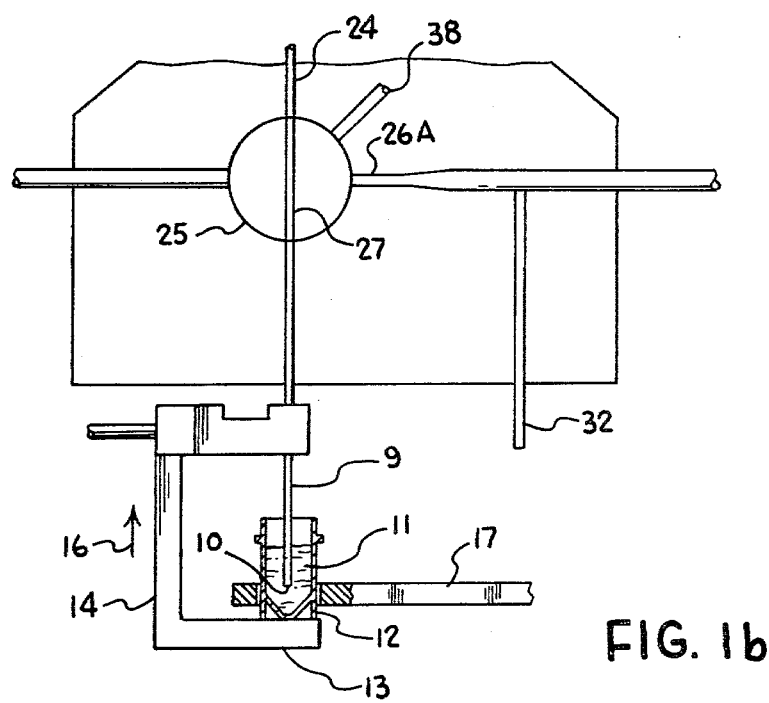
FIG. 1b

POS. 2

POS. 1

POS. 3

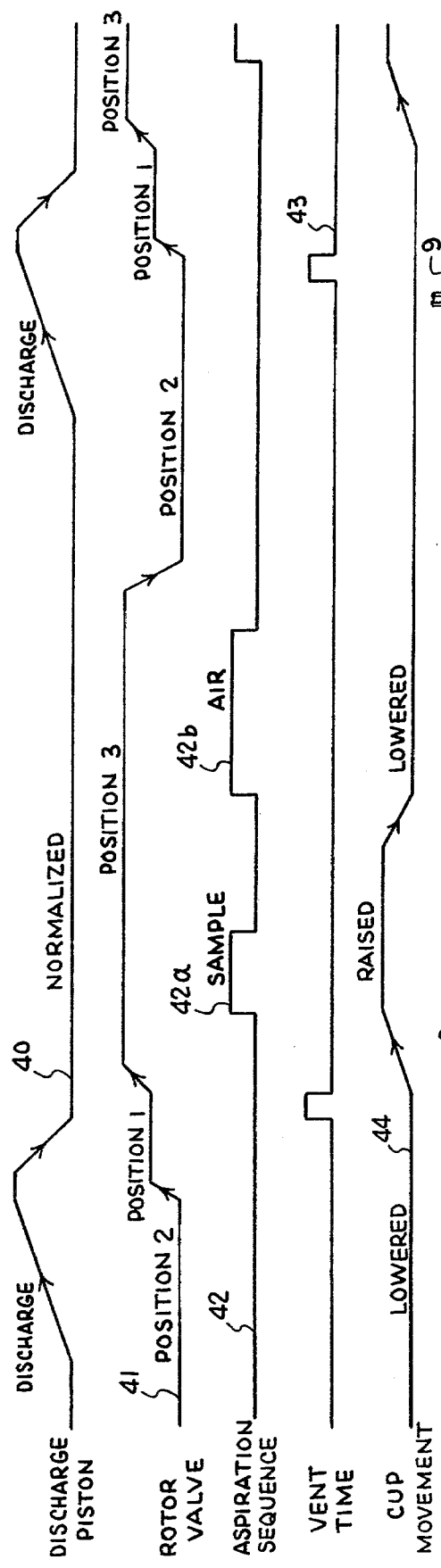
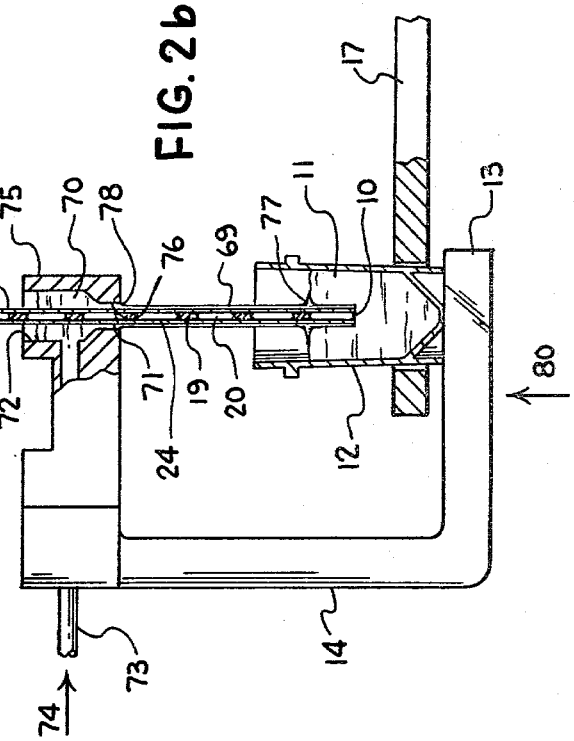
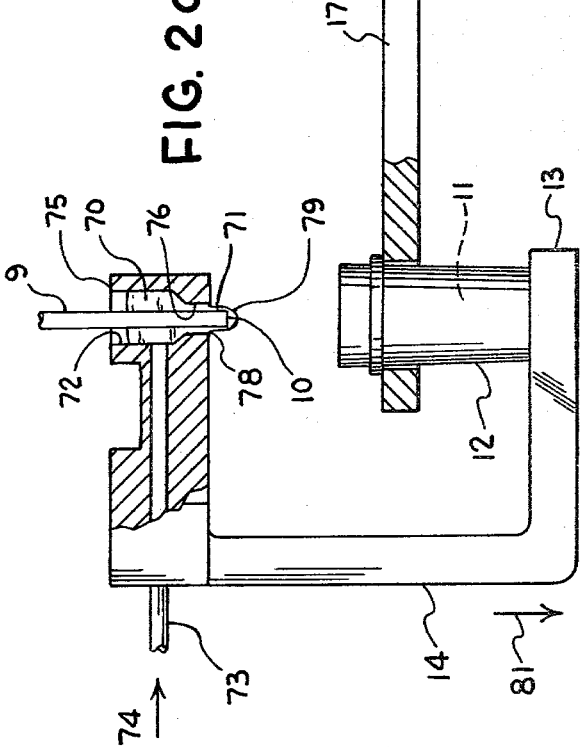

METERING DEVICE

BACKGROUND OF THE INVENTION

1. Field of the Invention

This invention relates to metering apparatus for aspirating discrete liquid samples, either for subsequent dispensing or passing to a continuous-flow analytical system, wherein contamination between successively aspirated samples is avoided.

2. Description of the Prior Art

In prior art metering apparatus, contamination between successively aspirated liquid samples has been a major problem. Such contamination can result, for example, from residue remaining on the probe surfaces from a previously aspirated liquid sample. The avoidance of contamination is of particular concern where liquid samples are successively aspirated, in precise volumes, for the analysis of different constituents of interest, for example, as described in the Skeggs et al U.S. Pat. No. 3,241,432, issued on Mar. 22, 1966, and in the Smythe et al U.S. Pat. No. 3,479,141, issued on Nov. 18, 1969, assigned to a common assignee. In such systems, contamination has been significantly reduced by aspirating a segment wash liquid between successive liquid samples, adjacent samples being separated by a sequence of air-wash liquid-air segments. To this end, the aspirating probe is immersed into a wash liquid reservoir between successive sample immersions, so as to remove contaminants from both the interior and peripheral probe surfaces. Also, U.S. Pat. No. 3,479,141 teaches that contamination between successive sample liquids in continuous-flow analytical systems is very significantly reduced by introducing a liquid, e.g., silicone oil, which is immiscible with the aqueous samples and preferentially wets the interior surfaces of the conduit system. In such event, the successive liquid samples are, in effect, encased within the immiscible fluid, and not in contact with the interior conduit surfaces.

Also, in the case of a metering system of the dispenser-type the aspirating probe is immersed into successive liquids, either samples or reagents, which are aspirated and dispensed, sequentially and in precise volumes. Such dispensing is effected by the use of a pilot fluid, which serves to "back-flush" contaminants from the interior surface of the probe system. Again, possible contamination resulting from residues on the peripheral probe surfaces has been avoided by immersing the probe into a wash liquid reservoir, and reverse-flushing such probe to remove contaminants from both the interior and peripheral probe surfaces. This need to actively wash the probe surfaces necessarily reduces the rate at which precise liquid volumes can be aspirated or dispensed, and, also, requires a more complicated probe-driving mechanism.

A system which has been found to be quite effective in eliminating contaminants is described in A. Reichler et al, U.S. Pat. No. 4,121,466, issued on Oct. 24, 1978, assigned to a common assignee. This system features flowing an immiscible liquid, e.g., silicone oil, over the surface of the aspirating probe, which liquid is aspirated intermediate successive sample aspirations. Such liquid selectively wets the interior and exterior surfaces of the probe and the interior surfaces of the conduit system, to prevent the deposit of aqueous sample residues upon such surfaces.

With the contemplation of high speed, miniaturized metering systems which aspirate, convey and rapidly deliver micro-amounts of aqueous fluid, the need has arisen to more precisely and uniformly control the application of the protective immiscible fluids to the probe and conduit surfaces.

The proposed invention contemplates the delivery of a plurality of one-lambda aliquots of aqueous fluid, such as plasma or serum, at a rate of one sample per second. In order to achieve this rigorous flow parameter, the probe and conduits of the invention require a uniform coating of immiscible fluid usually in thicknesses of several microns. Naturally, the application of such minute amounts of immiscible fluid to the miniaturized probe surface requires extremely precise application and control. The system described in the aforementioned patent to A. Reichler et al, U.S. Pat. No. 4,121,466, teaches a random, non-uniform flow of immiscible fluid over the outer probe surface under the influence of gravity forces. This coating technique is not precise enough to meet the continuity and uniformity requirements of the present metering system. The invention, therefore, is an improvement over the Reichler et al system, and features the direct application of the immiscible fluid to the surface of the probe in a uniform and precisely controlled manner.

SUMMARY OF THE INVENTION

The invention relates to a system for the metering of aqueous samples, such as serum or plasma, which comprises an aspirating probe having an inlet end. An applicator directly surrounds the probe in substantially contiguous fashion and layers a very thin uniform film or layer of immiscible fluid upon an outer surface of the probe.

The applicator is moved relative to the probe, so as to layer such immiscible fluid layer upon the outer probe surface. An aspirating mechanism connected to the probe alternately aspirates a controlled volume of aqueous sample, when the probe is immersed therein, and air along with some immiscible fluid coated upon the outer surface of the probe, when the probe is withdrawn from the sample. Accordingly, alternating sample and air segments encased within the immiscible fluid, as hereafter described, are passed along the probe. A rotary-type valve transfers each aspirated aqueous sample, in turn, from the probe to a conduit for dispensing, e.g., to an analytical system. While located in the valve, each aqueous sample is bracketed by air segments to preserve the integrity of the fluid sample segment and prevent contamination between successive samples passed therethrough.

It is an object of this invention to provide an improved fluid metering system;

It is another object of the invention to provide a fluid metering system which is free of contamination;

It is a further object of this invention to provide a high speed miniaturized metering system;

It is still another object of the invention to provide a contaminant-free fluid metering system with an improved aspirating rate.

These and other objects of this invention will be better understood and will become more apparent with reference to the following detailed description taken in conjunction with the accompanying drawings.

BRIEF DESCRIPTION OF THE DRAWINGS

FIG. 1a is a schematic diagram of the metering system of this invention in a non-aspirating position;

FIG. 1b is a schematic diagram of such metering system in a sample aspirating position;

FIGS. 2a and 2b are enlarged schematic views of the applicator and probe of such metering system;

FIG. 3 is a timing diagram for such metering system; and

FIGS. 4 and 5 illustrate schematic perspective views of alternate embodiments of the applicator of FIGS. 2a and 2b.

DETAILED DESCRIPTION OF THE INVENTION

Figure 1C:
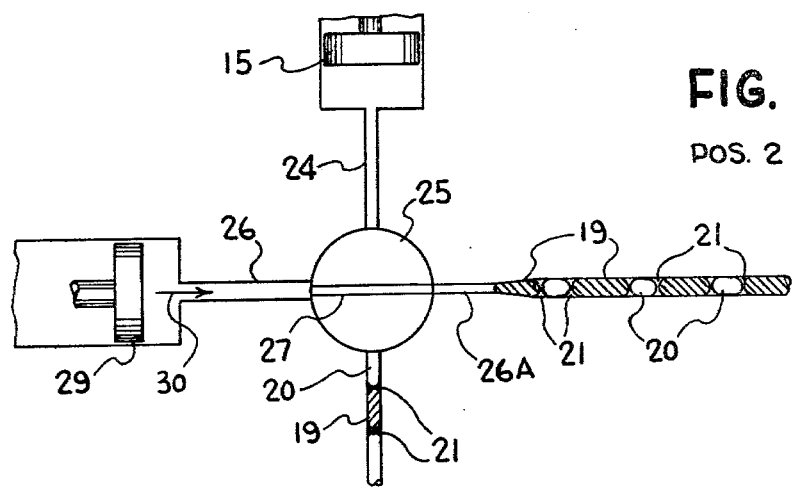
FIG. 1c is a schematic diagram of the rotor of such metering system in a sample dispensing position.

Referring to FIG. 1a, the metering system of this invention is shown in a schematic diagram. The system comprises a fixedly mounted probe 9, having an inlet portion 10 for immersion into an aqueous sample 11 contained in a sample cup 12. The sample cup 12 is shown resting upon a lower leg 13 of a "C"-shaped support 14.

The cup 12 is one of a plurality of sample cups (not shown), which are each supported in a well 18 defined in an indexing table 17. The table 17 is periodically indexed to bring each cup 12 beneath the fixed probe 9. When the cup 12 is indexed below the probe 9, it comes to rest upon (or is positioned slightly above) leg 13 of the "C"-shaped support 14, as aforementioned.

When the cup 12 has been indexed, the "C"-shaped support 14 is moved upward, as shown by arrow 16 in FIG. 1b. When support 14 moves to this upper position, the leg 13 lifts the cup 12 from the index table 17, such that the inlet 10 of the probe 9 is immersed into the sample 11 in cup 12. The sample 11 is drawn into the inlet 10 of probe 9 by the aspirating piston 15.

After the sample is aspirated, the "C"-shaped support 14 is lowered to its original position (FIG. 1a), and a new sample cup 12 is indexed beneath probe 9. In this manner, segments 19 of samples 11 are successively introduced into the inlet 10 of probe 9. Piston 15 is operated in stepped fashion to precisely control the aspirated sample volume, e.g., a one-lambda (microliter) is drawn into the probe 9. While the probe 9 is not immersed in a sample cup 12, piston 15 is further stepped to aspirate both air and immiscible fluid, the latter having been applied to the outer surfaces of the probe 9 by the applicator or wiper arm defined by bore 76 of housing 75 (FIGS. 2a & 2b), as hereinafter described. The successive sample segments 19 are successively spaced from each other by air segments 20 and immiscible fluid segments 21, the immiscible fluid encapsulating both the air segments and sample segments, as more particularly described in U.S. Pat. No. 3,479,141, cited above. Thus, an interdigitated flow pattern is created along the probe 9, as illustrated in FIG. 1f.

A rotary selection valve 25 is disposed in the conduit line 24 of probe 9 between aspirating piston 15 and the probe inlet 10. A storage tube 27 disposed within the rotor of valve 25 acts as a fluid connection between probe 9 and aspirating piston 15. Piston 15 operates such that a sample segment, previously aspirated, is substantially centrally disposed within storage tube 27. Selection valve 25 serves to transfer each successive sample segment 19 aspirated in probe 9 intact to conduit 26A, which is in fluid communication with analyzing station 34. Each sample segment 19, when positioned in storage tube 27, is sandwiched between two adjoining immiscible fluid segments 21 and air segments 20. The adjoining air segments 20 are sheared when the rotor of valve 25 is rotated, thus leaving the sample segment 19 isolated but intact within the storage tube 27 of valve 25, and contamination between successive sample segment is avoided.

Figure 1D:
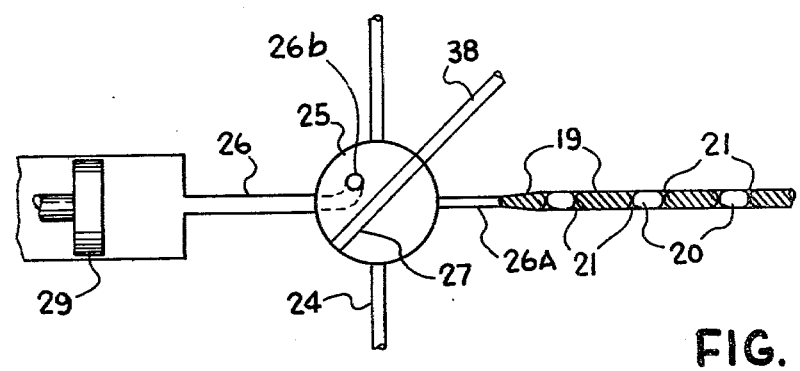
FIG. 1d is a schematic diagram of the rotor of such metering system in a venting position.
Figure 1F:
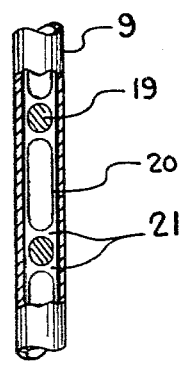
FIG. 1f is an enlarged sectional view of the probe of the metering system of FIG. 1a, showing the developed flow pattern between the aspirated sample, air and immiscible fluid.
Figure 1E:
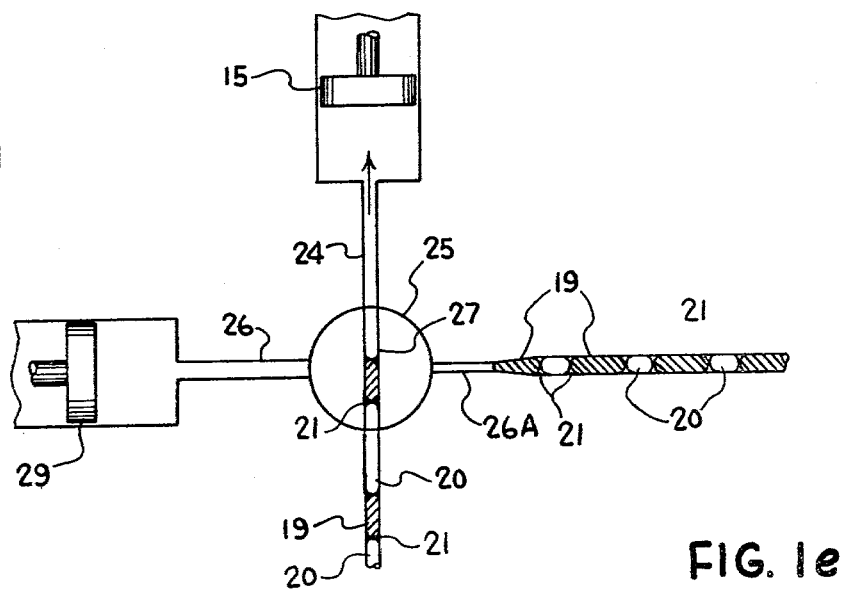
FIG. 1e is a schematic diagram of the rotor of such metering system in a sample aspirating position.

Valve 25 is rotated clockwise from the position illustrated in FIG. 1a, in turn, to two other positions designated "1" (FIG. 1d) and "2" (FIG. 1c), respectively, thus shearing the two air segments 20 extending across the boundaries of storage tube 27 and isolating the sample segment in storage tube 27. In position "2" (FIG. 1c), the storage tube 27 acts as a bridge for conduit 26, and discharging piston 29, which is operated to inject the sample segment, as illustrated by arrow 30 in FIG. 1c, along with the bracketing air segments along conduit 26A. After each sample segment 19 is transferred to conduit 26A, it is advanced intermittently, by the injection of subsequent sample segments, until it reaches Junction A, whereat it is entrained in a continuous stream of diluent from ancillary injection line 32, which is in fluid communication with the conduit 26 as depicted in FIGS. 1a and 1b. The length of conduit 26A is such as to insure that each sample segment 19 appearing at Junction A is rapidly entrained in the continuously flowing diluent stream. The diluted sample segment 19 is passed along conduit 26A, and reagent from a reagent station 33 is added to the sample, so as to react the same in respect of a particular analyte, which reaction is analyzed at analyzing station 34.

After each discharge of a sample segment 19 from the rotary valve 25 to the conduit 26A, the rotary valve 25 is turned to position "1" and discharging piston 29 is reduced to atmospheric pressure. In this position, the emptied storage tube 27 is placed in communication with venting port 38, which allows any pressure in tube 27 to be normalized, before returning valve 25 back to the aspirating position, as illustrated in FIG. 1, to receive the next sample segment 19.

The operating sequence between the movement of cup 12, the aspiration of immiscible fluid, air and sample segments, the operation of rotary valve 25, and the injection of sample segments 19 from such valve 25 to conduit 26A, is illustrated in the timing diagram of FIG. 3.

The timing diagram of FIG. 3 shows five distinct timing lines 40, 41, 42, 43, and 44, respectively. Line 44 depicts the movement cycle of cup 12 and line 42 depicts the sample aspiration cycle. When a cup 12 is in the upper position (FIG. 1b), the sample 11 in the cup 12 is aspirated as illustrated by line 42a. At the same time, it is observed that the rotary valve is in the aspirating position "3". When sample segment 19 has been aspirated by probe 9, the cup 12 is lowered, as shown in line 44. Coincident with the lowering of the cup, an air segment and a controlled volume of immiscible fluid are aspirated, as illustrated by line 42b.

After a sample segment 19 and an air segment 20 and immiscible fluid 21 have been aspirated into probe 9, the rotary valve 25 is switched from position "3" to position "2" and into fluid communication with conduit 26, as depicted in line 41. The sample and air and immiscible fluid segments 19, 20 and 21, respectively, previously aspirated, displace a previously aspirated sample segment 19, along with bracketing air and immiscible fluid segments 20 and 21 from the probe 9 into valve 25, so as to be disposed in storage tube 27 of valve 25 for injection into conduit 26A. The injection of sample segment 19, so disposed, into conduit 26A is illustrated by the discharge cycle of piston 29 in line 40.

After the sample segment 19 has been injected into conduit 26A, rotary valve 25 is switched to position "1" (line 41) to allow venting (line 43), and the pistons 29 and 15 are reset. Line 26 is pressurized through port 26b in valve 25 (FIG. 1d) to prevent back flow of a subsequent aspirated sample into line 26 when the valve 25 is switched to position 2 (FIG. 1c). During venting, any pressure in storage tube 27 is reduced to atmospheric pressure along venting port 38. When the venting is terminated, rotary valve 25 returns to position "3" and a next sample cup 12 is raised to immerse probe 9 (line 44) and initiate a next sample aspiration cycle.

Reference is now made to FIGS. 2a and 2b, which are enlarged sectional views of the oil applicator mechanism, which applies a thin controlled film of immiscible fluid, e.g., silicone oil, over the outer surface of probe 9. The applicator mechanism features an immiscible fluid reservoir 70 which is supplied (arrow 74) with immiscible fluid along conduit 73. Reservoir 70 is defined by a bore 72 in housing 75, which is integrally formed in "C"-shaped support 14.

The probe 9 is aligned axially through the bore 72 and reservoir 70 into still a smaller bore 76 defined in the base of housing 75. The clearance between bore 76 and the outer probe surface 71 is only a few thousandths of an inch wide (a capillary-type fit). As such, there is minimal, if any, flow by gravity of the immiscible fluid in reservoir 70 down the sides (outer surfaces) 71 of the probe 9 but, rather, the immiscible fluid is retained in bore 76. Because of such capillary-type fit, the immiscible fluid, e.g., oil, forms a meniscus at the lower edge 78 of housing 75 and the opposing surface portions of probe 9. To prevent overflowing of bore 72, the immiscible fluid is metered to reservoir 70 at an appropriate rate.

The immiscible fluid is applied to the outer surface 71 of probe 9 by a wiping action of the surface of bore 76 over the outer surface 71 of the fixedly mounted probe 9 during relative movement of such probe and the bore 76 of housing 75.

Referring to FIG. 2a, the housing 75 which forms an integral part of "C"-shaped support 14 is at a lower position of travel with respect to the fixedly mounted probe 9. When a sample 11 is to be aspirated, support 14 is raised (arrow 80), thus causing a thin, uniform layer 69 of the immiscible fluid to be wiped over the outer surface 71 of probe 9, as illustrated in FIG. 2b.

The cup 12 which rests upon the lower leg 13 of support 14, is simultaneously raised with the wiping of the immiscible fluid upon the probe 9, to immerse the inlet 10 of the probe within sample 11. Thus, just prior to every sample aspiration, the outer surface 71 of the probe 9 receives a fresh layer 69 of the immiscible fluid to prevent portions of the aqueous sample 11 from depositing upon, adhering to, or otherwise contaminating such surface. As the probe 9 is immersed into sample 11, a portion of layer 69 of immiscible fluid layered upon surface 71 is skimmed, but not wiped clean from probe 9, by a stripping action resulting from such immersion. A pool 77 of wiped immiscible liquid forms about the probe 9, due to the interplay of surface forces comprising the surface forces of the fluids with respect to each other in combination with the wetting forces of the immiscible fluid with respect to the probe surface. When the sample cup 12 is withdrawn from probe 9, as when support 14 is lowered (arrow 81), such pool 77 forms a small globule 79 of immiscible fluid over the inlet 10 of probe 9, inasmuch as it preferentially wets the probe material to the substantial exclusion of the aqueous sample.

The formation of globule 79 is further assisted, in part by a slight flow of immiscible fluid down the surface 71 resulting from the downward wiping action of bore 76.

When air is aspirated into the probe inlet 10, the globule 79 of immiscible fluid is also drawn into the probe conduit 24. The aspirated immiscible fluid has an affinity for the probe surfaces to the exclusion of the air and sample segment, and coats the inner walls of the conduit 24, such that the successive air and sample segments are encapsulated within the immiscible fluid. The encapsulating air and sample segments 19 and 20, respectively, are thus prevented from contacting the conduit surfaces and the problem of contamination between successive sample segments 19 is avoided.

Now referring to FIG. 4, an alternate embodiment for layering layer 69 of immiscible fluid upon surface 71 of probe 9 is illustrated. In place of reservoir 70 and bore 76, a small hollow torus 90 surrounds probe 9 and is integral with support 14. The torus 90 has small jet holes or orifices 92 defined in its inner wall 91. Immiscible fluid is introduced into torus 90 along the aforementioned conduit 73, so as to produce a very fine mist of immiscible fluid directed over the probe surface 71 in precise fashion. The flow of immiscible liquid along conduit 73 is controlled to spray a precise amount of the immiscible fluid over the outer surface 71 of the probe 9, such that the fluid will not flow down by gravity over the outer surface 71 of the probe. The flow of immiscible fluid along conduit 73 may be discontinuous so as to spray probe surface 71 only during the upward movement of support 14.

Another embodiment of the applicator mechanism shown in FIG. 5, depicts a sponge disc 95 in surrounding contiguous contact with surface 71 of probe 9 and integral with support 14. The sponge disc 95 is fed with and saturated by immiscible fluid from the aforementioned conduit 73, and thoroughly absorbs the immiscible fluid so as to completely coat the surface 71 of probe 9 with a very precise layer of immiscible fluid, when moved relative to surface 71 of probe 9. As in the case of FIG. 4, the flow of immiscible fluid along conduit 73 may be discontinuous.

The outer surface 71 of the probe 9 comprises a Teflon compound which is compatible with, and has an affinity for the immiscible fluid which can be a silicone or fluorocarbon oil.

Having thus described the invention, what is desired to be protected by Letters Patent is presented in the following Appended Claims.

What is claimed is:

1. A metering system for aqueous samples, comprising:
  a tubular probe having an inlet and inner and outer surfaces;
  aspirating means in fluid communication with said probe;

means for immersing at least a portion of said probe into successive aqueous samples;

applicator means for directly applying a fluid to at least that portion of said outer surface of said probe which is to be immersed within said successive samples, said fluid being characterized as immiscible with respect to said successive samples and as preferentially wetting said probe to the substantial exclusion of said aqueous samples; and means for relatively moving said applicator means and said probe with respect to each other to apply a thin layer of said fluid over at least said outer surface portion of said probe.

2. The metering system of claim 1, wherein said probe is fixedly mounted, said moving means being operative to move said applicator means relative to said probe.

3. The metering system of claim 2, wherein said applicator means is movable by said moving means over said outer surface of said probe a distance traversing to substantially the inlet end of said probe.

4. The metering system of claim 2, further comprising a sample cup for containing each of said samples, said immersing means being operative to move each sample cup to immerse said probe inlet into said sample.

5. The metering system of claim 4, further comprising an indexing table for successively moving each sample cup with respect to said fixedly mounted probe preparatory to immersion of said probe therein.

6. The metering system of claim 4, wherein said aspirating means is operative to aspirate, at least, an air segment between aspirations of said successive samples, said immiscible liquid being further characterized as preferentially wetting the inner surface of said probe to the substantial exclusion of said aspirated sample and air segments.

7. The metering system of claim 6, wherein a portion of said fluid applied to the outer surface of said probe is accumulated about the inlet end of said probe, said aspirating means further operative to aspirate said accumulated fluid.

8. The metering system of claim 1, wherein said aspirating means is operative in discontinuous fashion to aspirate a controlled volume of each of said successive samples while said probe is immersed in each sample.

9. The metering system of claim 1, wherein said applicator means is concentrically arranged about the outer surface of said probe.

10. The metering system of claim 1, wherein said applicator means comprises a housing defining a reservoir for containing said fluid, said probe passing through said reservoir and a bore defined in a base portion of said housing, the clearance between opposing surfaces of said bore and said probe being such as to substantially preclude flow of said fluid from said reservoir.

11. The metering system of claim 10, wherein said moving means is operative to relatively move said probe axially along said bore.

12. An improved fluid metering system, comprising:
a tubular probe having an inlet for immersion into successive fluid samples;
aspirating means in fluid communication with the said probe for aspirating into said probe segments of said successive fluid samples bracketed by air segments;
a conduit associated with said probe for receiving said fluid sample segments in turn from said probe; and
a selector disposed between said probe and said conduit for receiving said sample segments in turn, and operative between first and second positions, said selector in said first position being in fluid communication between said probe and said aspirating means for receiving and storing said sample segments in turn, said selector in said second position being in fluid communication with said conduit for transferring said stored sample segments in turn to said conduit.

13. The fluid metering system of claim 12, wherein said selector comprises a rotor rotatively movable between said first and second positions, said rotor defining a storage tube, and said aspirating means being operative to locate an air-bracketed sample segment within said storage tube, such that the bracketing air segments are sheared without disturbing said sample segment in said storage tube when said rotating rotor is moved from said first position to said second position.

14. The metering system of claim 13, wherein said rotor is movable to a third position, to connect said storage tube to a venting port for reducing the pressure in said storage tube.

15. The metering system of claim 12, further comprising means disposed along said conduit for diluting said successive sample segments.

16. The metering system of claim 16, further comprising a reagent station disposed along said conduit for reacting said successive sample segments.

17. The metering system of claim 16, further comprising an analyzing station disposed along said conduit for analyzing said reaction.

18. The metering system of claim 17, further comprising means for passing said reacted successive sample segments as a continuously flowing stream through said analyzing station.

19. The metering system of claim 12, further including means for supplying an immiscible fluid at said inlet of said probe, said fluid being characterized as preferentially wetting an inner surface of said probe to the substantial exclusion of said aspirated sample and air segments, said aspirating means being operative to aspirate said immiscible fluid whereby said sample and air segments passed along said probe and conduit are encapsulated within said fluid to prevent contamination between successive sample egments.

* * * * *